United States Patent [19]

Denton, Jr. et al.

[11] Patent Number: 4,492,777

[45] Date of Patent: Jan. 8, 1985

[54] HEAT TREATED BARIUM OR STRONTIUM GLASS

[75] Inventors: Robert K. Denton, Jr., Allentown; Narayan G. Kumar, Freehold, both of N.J.

[73] Assignee: Johnson & Johnson Dental Products Co., East Windsor, N.J.

[21] Appl. No.: 444,560

[22] Filed: Nov. 26, 1982

[51] Int. Cl.$^3$ .................. C08K 3/40; C03B 32/00
[52] U.S. Cl. .................. 523/115; 106/306; 523/116; 523/117

[58] Field of Search .................. 523/115, 116, 117; 106/306; 65/111

[56] References Cited

U.S. PATENT DOCUMENTS

| | | | |
|---|---|---|---|
| 4,150,485 | 4/1979 | Kee et al. | 523/115 |
| 4,220,582 | 9/1980 | Orlowski et al. | 523/116 |
| 4,297,266 | 10/1981 | Ibsen et al. | 523/117 |
| 4,336,153 | 6/1982 | Maries et al. | 523/116 |

*Primary Examiner*—Lewis T. Jacobs

[57] ABSTRACT

The affinity for water of acid-washed barium or strontium glass powder is reduced by a heat treatment.

4 Claims, No Drawings

HEAT TREATED BARIUM OR STRONTIUM GLASS

The invention relates to a process for heat treating barium or strontium glass to reduce the hydrophilic nature of said glass, to the barium or strontium glass so treated, and to dental composite compositions which utilize said barium or strontium glass as a filler.

BACKGROUND OF THE INVENTION

Barium and/or strontium glass powder is widely used as a filler in dental restorative resinous compositions because it imparts radiopacity to such compositions. Such resin-based dental filling materials have found limited use, however, for the filling of cavities on the grinding surfaces of molars. The reason for this is that such compositions have been found to have inadequate wearing properties to withstand the stresses which are normal in such areas. Among the factors that contribute to the inadequate wear properties of prior art resinous dental restorative dental compositions are microfractures of the overall composite, and debonding that occurs at the filler/polymer matrix interface. Both of these are most likely to occur during the cyclic loads encountered while chewing in an aqueous environment with attendant modest temperature fluctuations. Inadequate hydrolytic stability appears to contribute to both the microfractures and debonding.

In U.S. patent application Ser. No. 404,262, filed Aug. 2, 1982, now abandoned, entitled "Dental Restorative Compositions Having Improved Mechanical Properties and Hydrolytic Stability", by Dr. N. G. Kumar, and assigned to the same assignee as this application, there is disclosed one approach to the production of dental restorative compositions having improved hydrolytic stability, resistance to debonding at the filler/polymer interface, and resistance to the formation and propagation of microfractures in the composite. One of the important features of the invention disclosed in said application is the use of relatively hydrophobic inorganic fillers. The hydrophobic nature of the fillers that are desired for use in that invention is measured by the amount of water that the filler will absorb when simply exposed to normal ambient atmospheric conditions.

This invention is directed to the provision of barium or strontium glass powder having enhanced hydrophobic properties, and hence, considerably enhanced utility in the preparation of dental restorative resinous compositions.

SUMMARY OF THE INVENTION

The invention provides a process for reducing the affinity of acid-washed barium or strontium glass powder to water, which comprises subjecting acid-washed barium or strontium glass powder to an elevated temperature (below the sintering temperature of the glass) and for a period of time sufficient to reduce the specific surface area of the glass powder. The invention also provides the glass powder produced by the process, and dental restorative compositions utilizing said glass powder as the filler.

THE PRIOR ART

Acid-washed barium glass powder is an article of commerce that is widely used as a filler in dental restorative compositions.

There are numerous patents that disclose the heating of glass bodies or fiber glass for various purposes, such as for coating the glass and for annealing the glass. For instance, reference is made to U.S. Pat. Nos. 3,093,508 and 3,511,697. Such patents rarely, if ever, mention the particular type of glass that is contemplated.

The above mentioned Kumar application, Ser. No. 404,262, discloses the subject claimed invention in brief outline. However, that application does not constitute prior art to this application because the invention claimed herein was disclosed by the inventor named in this application to Dr. Kumar.

DETAILED DESCRIPTION OF THE INVENTION

The glass powder that is employed in this invention is acid-washed barium or strontium glass.

The glass employed contains, as essential ingredients, barium oxide and/or strontium oxide, and silicon dioxide. The glass may also contain other metal oxides such as aluminum oxide, boron oxide, and the like. Apparently, the glass should be substantially free of alkali metal oxides such as sodium oxide and potassium oxide, as well as calcium oxide and magnesium oxide. The glass is preferably a single phase glass. If the mole percent of barium oxide or strontium oxide exceeds a certain point, the glass becomes two-phased. This proportion can vary, depending on the presence and proportion of other metal oxides in the glass. For glasses composed of oxides of barium, silicon, boron, and aluminum, this upper limit for a single phase glass is about 20 mole percent barium oxide. The relevant proportion for other glasses contemplated for use in the invention can be determined by routine experimentation. One preferred glass for use in the invention has the following composition:

$SiO_2$—67 mole percent
BaO—16.4 mole percent
$B_2O_3$—10 mole percent
$Al_2O_3$—6.6 mole percent The minimum barium and/or strontium content of the glass is preferably that which imparts radiopacity to the glass.

The powders contemplated for use in this invention are glass powders, produced by known procedures, and generally having particle sizes within the range of from sub-micron to about 100 microns.

The acid-washing treatment to which the glass powder is subjected is carried out by known procedures. For instance, a mixture of 1 part (by weight) of glass powder, 1 part of 37 percent aqueous hydrochloric acid, and 1 part of de-ionized water is stirred at room temperature for 45 minutes, filtered, and rinsed with de-ionized water until the pH of the filtrate is the same as the rinse water. The powder is then dried at about 50° C. overnight in a forced air oven. The acid wash is used to remove metal impurities from the glass, to reduce the amount of leachable barium or strontium from the surface of the glass, and to add surface area to the glass to provide additional sites for bonding by silane coupling agents.

In accordance with the invention, the acid-washed glass powder is subjected to a heat treatment to reduce the affinity of the glass powder for water. This heat treatment is carried out at an elevated temperature below the sintering temperature of the glass powder (the sintering temperature can be determined by known procedures, as by thermo-mechanical analysis "TMA"), but high enough to cause a significant reduction in the specific surface area of the glass powder, as measured by known procedures such as by a "Quantasorb" B.E.T. surface area analyzer. The reduction in specific surface area will usually be at least about 50 percent (i.e., the surface area of the heat treated glass powder will be less than about one-half that of the untreated powder), up to 80 to 90 percent, or even more in some cases. The heat treatment time is not at all critical in that it need be carried out only for the minimum time needed to heat all the powder to the desired temperature. Apparently the effect of the heat on the glass powder is quite rapid, and all that is required is to bring all of the mass of powder up to the desired temperature. However, since the glass powder is an excellent heat insulator, this can take several hours for masses of powder wherein the heat must travel through a significant thickness of powder to heat all of the glass to the desired temperature. The examples, below, present a specific illustration of the required treatment time for one specific mass of power in a container of a specific shape.

The heat treatment described above reduces the hydrophilic nature of the glass powder such that, when the glass is exposed to normal ambient conditions, it will absorb less than 0.1 weight percent water. ("Normal ambient conditions" are, for example, 20° to 30° C. and 20 to 40 percent relative humidity.) The water content is determined by a differential scanning calorimeter ("DSC"). The first departure from baseline in a DCS scan is caused by the presence of water. To determine the amount present, the area under the peak is determined and normalized relative to the weight of the sample.

To enhance the utility of the heat treated barium glass powder of this invention for use in reinforcing resinous compositions, a coupling agent can be used to improve the bond between the filler and the resin. Such coupling agents include gamma-methacryloxypropyltrimethoxysilane.

The invention is illustrated by the examples below.

EXAMPLE 1

The glass powders used in this example and in Example 2 had the following composition:
 $SiO_2$—67 mole percent
 BaO—16.4 mole percent
 $B_2O_3$—10 mole percent
 $Al_2O_3$—6.6 mole percent
A 0—13μ particle size batch of this glass powder had the following particle size analysis:
 100% below 13μ
 55% below 5μ
 18% below 2μ
The raw glass powder, prior to acid wash, has a specific surface area of about $0.8 \pm 0.1$ m²/gm. After acid-washing as described above, the specific surface area is about $10 \pm 2$ m²/gm.

Five kilograms of the acid-washed powder are placed in a saggar crucible. The crucible is cylindrical, about 12 inches in diameter and 10 inches high. Five kilograms of the powder nearly fill the crucible. The crucible containing the powder is placed in an oven, which is set at 650° C. It takes about 16 hours for the entire mass of powder to heat up to 650° C. After 16 hours, the furnace is turned off and the powder is slowly cooled to room temperature. The specific surface area of the heat treated glass is about $3.5 \pm 1$ m²/gm.

EXAMPLE 2

The enhanced performance of heat treated barium glass as a reinforcing filler for dental composite materials is illustrated in this example.

In this example, the following materials were used:
Bisphenol-A dimethacrylate ("BADM")
Ethoxylated bisphenol-A dimethacrylate ("EBDM")
Methacrylic acid ("MAA")
2,2'-propane bis[3-(4-phenoxy)-1,2-hydroxypropane-1-methacrylate] ("Bis-GMA")
Tetraethylene glycol dimethacrylate ("TEGDM")
2-(N,N-dimethylamino)ethyl methacrylate ("DMAEMA")
Filler A—Conventional acid-washed 0–13μ barium glass powder having the following particle size analysis (by Coulter Counter):
 100% below 13μ
 55% below 5μ
 18% below 2μ
Water content, by DSC, was 1.05 weight percent
Filler B—Same 0–13μ glass powder as Filler A, but heated to 650° C. for sixteen hours, as described in Example 1. The water content, by DSC, was 0.05 weight percent. The water contents are determined on the fillers prior to treatment with silane. The barium glass fillers were treated with A-174 silane (gamma-methacryloxypropyltrimethoxysilane), Filler A with 3 weight percent and Filler B with 1 weight percent (the heat treated glass requires less silane coupling agent because it has a lower specific surface area than the non-heat treated glass).

A series of filled resin systems, formulated to be useful as dental composites, were prepared. The composite formulations were prepared by mixing fillers into the resins using a mini-Hobart (drill) mixer until a smooth paste resulted. The pastes were then placed in a vacuum oven and de-gassed at about 4 mm. mercury pressure until they were void-free, as determined by microscopic examination. Flexural test samples were made by placing the uncured filled resins in "Teflon" molds between glass slides, and exposing each side to 60 seconds exposure from a 75 watt/12 volt quartz projector lamp. All samples were aged for 24 hours at 37° C. in deionized water. Ten samples of each composite were tested for initial flexural strength, and ten additional samples were placed in pressure bottles with 300 ml. of deionized water, and were held at about 5 atmospheres and 145° C. for 7 days. After this time, they were removed from the bottles and tested for flexural strength, using an Instron HP-11 stress-strain testing apparatus.

Table I displays the formulations and Table II displays the results of the flexural testing.

TABLE I

| | Parts by weight |
|---|---|
| Resin A | |
| Bis-GMA | 61.2 |
| BADM | 6.8 |
| TEGDM | 26.9 |
| MAA | 2.0 |
| Benzil | 0.3 |
| Camphorquinone | 0.3 |
| DMAEMA | 2.5 |
| Viscosity - 2560 cps | |
| Water Absorption[1] - 2.34 mg/cm² (0.01)[2] | |
| Resin B | |
| EBDM | 96.9 |
| Camphorquinone | 0.3 |
| Benzil | 0.3 |

TABLE I-continued

| | Parts by weight |
|---|---|
| DMAEMA | 2.5 |
| Viscosity - 2240 cps | |
| Water Absorption - 0.41 mg/cm$^2$ (0.01) | |
| Composite A | |
| Resin A | 28 |
| Filler A | 72 |
| Composite B | |
| Resin A | 28 |
| Filler B | 72 |
| Composite C | |
| Resin B | 28 |
| Filler A | 72 |
| Composite D | |
| Resin B | 28 |
| Filler B | 72 |

[1] The water absorption was determined on the cured, unfilled resins by ADA Specification No. 27 - immersion in water at 37° C. for seven days.

[2] The numbers in parentheses after the test data are the standard deviations.

TABLE II

| Composite | Initial Strength (N/mm$^2$) | Flexural Strength Pressure Boiled 7 days | % Loss | Water Absorption[3] mg/cm$^2$, 7 days at 37° C. |
|---|---|---|---|---|
| A (hydrophilic resin) (hydrophilic filler) | 111.0 (13.4) | 30.4 (7.9) | 72.6 | 1.23 (0.03) |
| B (hydrophilic resin) (hydrophobic filler) | 108.3 (10.6) | 46.4 (8.9) | 56.2 | 1.07 (0.03) |
| C (hydrophobic resin) (hydrophilic filler) | 109.6 (13.7) | 66.7 (9.9) | 39.1 | 0.44 (0.03) |
| D (hydrophobic resin) (hydrophobic filler) | 111.6 (10.7) | 78.6 (9.9) | 29.6 | 0.29 (0.02) |

[3] Water absorption on the filled composites.

What is claimed is:

1. A single phase barium or strontium glass powder produced by a process that comprises subjecting acid-washed single phase barium or strontium glass powder to an elevated temperature sufficient to cause a significant reduction in the specific surface area of said glass powder, but below the sintering temperature of said glass powder, wherein said glass is hydrophobic as is evidenced by its absorbing less than 0.1 weight percent water, as determined by a differential scanning calorimeter, when exposed to normal ambient conditions.

2. The glass powder of claim 1 wherein said powder is a barium glass containing up to about 20 mole percent barium oxide.

3. A resinous dental restorative composition containing a polymerizable composition, a polymerization initiator, and the glass powder of claim 1.

4. A resinous dental restorative composition containing a polymerizable composition, a polymerization initiator, and the glass powder of claim 2.

* * * * *